US011503995B2

United States Patent
Wang et al.

(10) Patent No.: US 11,503,995 B2
(45) Date of Patent: Nov. 22, 2022

(54) OPHTHALMOLOGIC APPARATUS

(71) Applicant: Topcon Corporation, Tokyo (JP)

(72) Inventors: Zhenguo Wang, Ridgewood, NJ (US); Zaixing Mao, Tokyo (JP); Kazuhiro Oomori, Tokyo (JP); Makoto Fujino, Tokyo (JP)

(73) Assignee: Topcon Corporation, Tokyo (JP)

( * ) Notice: Subject to any disclaimer, the term of this patent is extended or adjusted under 35 U.S.C. 154(b) by 207 days.

(21) Appl. No.: 16/845,747

(22) Filed: Apr. 10, 2020

(65) Prior Publication Data

US 2020/0337551 A1    Oct. 29, 2020

Related U.S. Application Data

(60) Provisional application No. 62/837,964, filed on Apr. 24, 2019, provisional application No. 62/837,900, filed on Apr. 24, 2019, provisional application No. 62/837,914, filed on Apr. 24, 2019, provisional application No. 62/837,844, filed on Apr. 24, 2019.

(51) Int. Cl.
    *A61B 3/10*          (2006.01)
    *A61B 3/00*          (2006.01)
    *A61B 3/15*          (2006.01)

(52) U.S. Cl.
    CPC ............ *A61B 3/101* (2013.01); *A61B 3/0008* (2013.01); *A61B 3/152* (2013.01)

(58) Field of Classification Search
    CPC ........ A61B 3/101; A61B 3/0008; A61B 3/152
    See application file for complete search history.

(56) References Cited

U.S. PATENT DOCUMENTS

| | | |
|---|---|---|
| 4,772,116 A | 9/1988 | Schroder et al. |
| 7,661,820 B2 | 2/2010 | Hara et al. |
| 7,758,190 B2 | 7/2010 | Korb et al. |
| 7,802,903 B1 * | 9/2010 | Wray .................. F21V 23/005 362/249.02 |
| 7,854,510 B2 | 12/2010 | Verdooner et al. |

(Continued)

FOREIGN PATENT DOCUMENTS

| | | | |
|---|---|---|---|
| EP | 1974657 A2 * | 10/2008 | ............ A61B 3/135 |
| EP | 2878259 A1 * | 6/2015 | ........... A61B 3/0025 |

(Continued)

*Primary Examiner* — William R Alexander
*Assistant Examiner* — Sharrief I Broome
(74) *Attorney, Agent, or Firm* — Chiesa Shahinian & Giantomasi PC

(57) ABSTRACT

An ophthalmologic apparatus includes: an objective lens that faces a subject's eye; a first illumination optical system that irradiates a cornea of the subject's eye with illumination light; and a corneal measurement optical system having an imaging element that takes an image of a corneal reflection light, which is a reflection of the illumination light, through the objective lens, and outputs an imaging signal. The corneal measurement optical system includes a first mirror arranged near the objective lens and a second mirror arranged near the imaging element. The first and second mirrors and are configured such that the corneal reflection light that enters and is reflected from the first mirror, and then enters and is reflected from the second mirror exits toward an incident side from which the corneal reflection light enters a reflection surface of the first mirror.

10 Claims, 5 Drawing Sheets

(56) References Cited

U.S. PATENT DOCUMENTS

| | | | |
|---|---|---|---|
| 7,988,294 B2 | 8/2011 | Korb et al. | |
| 2014/0286019 A1* | 9/2014 | Araki | F21V 5/04 |
| | | | 349/193 |
| 2021/0106224 A1* | 4/2021 | Zhou | G02B 21/0012 |

FOREIGN PATENT DOCUMENTS

| | | | | |
|---|---|---|---|---|
| JP | S61-500649 A | | 4/1986 | |
| JP | H07-136120 A | | 5/1995 | |
| JP | 2008-011983 A | | 1/2008 | |
| JP | 4624122 B2 | | 2/2011 | |
| JP | 5651119 B2 | | 1/2015 | |
| JP | 5665181 B2 | | 2/2015 | |
| WO | WO-2008062527 A1 | * | 5/2008 | ............... A61B 3/12 |
| WO | WO-2011066065 A1 | * | 6/2011 | ............. A61B 1/313 |

* cited by examiner

OPHTHALMOLOGIC APPARATUS

BACKGROUND

The present disclosure relates to an ophthalmologic apparatus, and more particularly, to an ophthalmologic apparatus that examines states of an anterior segment and tear fluid film of a subject's eye.

There has been known an ophthalmologic apparatus that irradiates a cornea of a subject's eye with illumination light, and observes a state of an anterior segment and an interference image formed by a tear fluid film of the cornea of the subject's eye to make a diagnosis of dry eye, for example.

Various types of arrangement of optical systems have been proposed as the ophthalmologic apparatus (Japanese Unexamined Patent Publication No. 2008-11983).

SUMMARY

However, the conventional optical system cannot sufficiently reduce unevenness in light intensity and/or chromatic aberration thereof, and a sensor receives part or all of a corneal image. As a result, an accurate image cannot be taken, which may make a precise measurement of a film thickness based on an interference image difficult.

The present disclosure has been made to solve the above-described problem, and it is therefore an object of the present disclosure to provide an ophthalmologic apparatus that reduces unevenness in light intensity and/or chromatic aberration of an optical system in an examination of a subject's eye, so that a thickness of a tear fluid film can be precisely measured.

An ophthalmologic apparatus of the present disclosure is an ophthalmologic apparatus including: an objective lens that faces a subject's eye; a first illumination optical system that irradiates a cornea of the subject's eye with illumination light; and a measurement optical system having an imaging element that takes an image of a corneal reflection light, which is a reflection of the illumination light, through the objective lens, and outputs an imaging signal. The corneal measurement optical system includes a first mirror arranged near the objective lens and a second mirror arranged near the imaging element. The first and second mirrors are configured such that the corneal reflection light that enters and is reflected from the first mirror, and then enters and is reflected from the second mirror exits toward an incident side from which the corneal reflection light enters a reflection surface of the first mirror.

The present disclosure provides an ophthalmologic apparatus that reduces unevenness in light intensity and/or chromatic aberration of an optical system in an examination of the subject's eye, so that a film thickness of a tear fluid film can be precisely measured.

DETAILED DESCRIPTION

Figure 1:
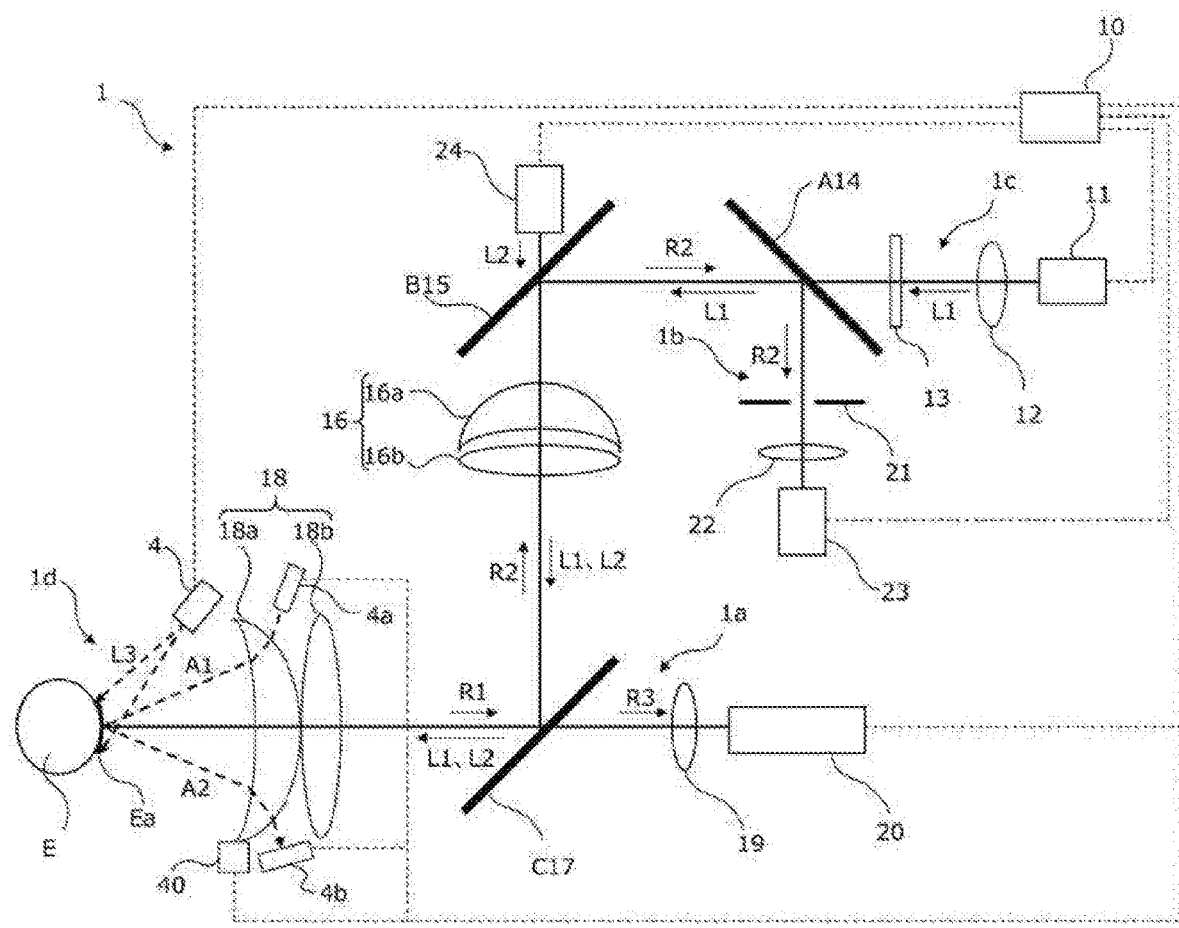
FIG. 1 is a schematic view illustrating an optical system of an ophthalmologic apparatus according to an embodiment of the present disclosure.

FIG. 1 is a schematic view illustrating an optical system of an ophthalmologic apparatus 1 according to an embodiment of the present disclosure. The optical system of the ophthalmologic apparatus 1 includes an anterior segment observation optical system 1a, a corneal measurement optical system 1b, a first illumination optical system 1c, and a second illumination optical system 1d.

The anterior segment observation optical system 1a includes a first lens group 18 of the present disclosure. The anterior segment observation optical system 1a includes a half mirror C17, a lens 19, and an anterior segment camera 20 that are arranged along the direction of an optical axis of the first lens group 18. Note that the term "half mirror" used herein refers to a reflecting mirror that splits light into reflected light and transmitted light at a branching ratio of approximately 1:1, but the present disclosure is not limited thereto.

The first lens group 18 is a so-called objective lens. In the present embodiment, the objective lens (first lens group 18) includes a plurality of lenses (18a, 18b), but the objective lens may include a single lens only. The first lens group 18 may allow the corneal surface of the cornea Ea of the subject's eye E to be irradiated with the illumination light emitted from the first illumination optical system 1c via the half mirror C17. Corneal reflection light R1, which is the reflection of the illumination light L1 from the corneal surface, enters the first lens group 18. This corneal reflection light enters the half mirror C17 from the first lens group 18.

The first half mirror C17 reflects part of illumination light L1 incident from the first illumination optical system 1c toward the first lens group 18. The half mirror C17 allows part (R3) of the corneal reflection light R1 incident from the first lens group 18 to pass therethrough and exit therefrom toward the lens 19, and reflects further part (R2) of the corneal reflection light R1 toward a second lens group 16, which will be described later.

The lens 19 allows the corneal reflection light R3 incident from the half mirror C17 to pass therethrough and exit therefrom toward the anterior segment camera 20. The anterior segment camera 20 includes a complementary metal oxide semiconductor (CMOS) or charge coupled device (CCD) imaging element, and takes an image of the corneal reflection light R3 incident from the lens 19 to output an imaging signal of an observation image of an anterior segment of the subject's eye E (hereinafter referred to as an "anterior segment observation image") to a controller (not shown).

The first illumination optical system 1c forms an optical path branching from the anterior segment observation optical system 1a via the half mirror C17.

The first illumination optical system 1c includes a first illumination light source 11. The first illumination optical system 1c further includes a lens 12, a filter 13, a half mirror A14 (second mirror), a half mirror B15 (first mirror), and a second lens group 16 which are arranged on an optical path of illumination light L1 emitted from the first illumination light source 11. The first illumination optical system 1c shares the half mirror C17 and the first lens group 18 with the anterior segment observation optical system 1a. In this manner, the first illumination optical system 1c forms an optical path branching from the anterior segment observation optical system 1a via the half mirror C17.

The first illumination light source 11 emits light. The first illumination light source 11 may be, for example, a light emitting diode (LED) light source or halogen lamp which emits white light, and emits white light as the illumination light L1 toward the lens 12. Alternatively, an LED having a different wavelength, a laser light source, or a combination of them may also be used. The lens 12 allows the illumination light L1 incident from the first illumination light source 11 to exit therefrom toward the filter 13. The filter 13 adjusts the light intensity and/or wavelength distribution of the illumination light L1 incident from the lens 12, and allows the illumination light L1 thus adjusted to exit therefrom toward the half mirror A14. Note that the LED may be a bullet-shaped LED. The LED may be replaced with a single halogen lamp or the like.

The half mirror A14 allows part of the illumination light L1 incident from the filter 13 to pass therethrough and exit therefrom toward the half mirror B15, and reflects the corneal reflection light R2 incident from the second lens group 16, which will be described later, toward the corneal measurement optical system 1b.

The half mirror B15 and the second lens group 16 allow the illumination light L1 incident from the half mirror A14 to exit therefrom toward the half mirror C17 described above. Further, the half mirror B15 and the second lens group 16 allow the corneal reflection light R2 incident from the half mirror C17 to exit therefrom toward the half mirror A14.

In this manner, the corneal surface of the cornea Ea is irradiated with, through the first lens group 18, the illumination light L1 emitted from the first illumination light source 11 and passing through the lens 12 and the first half mirror C17. As a result, the corneal reflection light R1, which is the reflection of the illumination light L1 from the corneal surface, enters the first lens group 18.

The corneal measurement optical system 1b forms an optical path branching from the first illumination optical system 1c via the half mirror A14. The corneal measurement optical system 1b shares the components from the first lens group 18 to the half mirror A14 with the first illumination optical system 1c, and also includes a diaphragm 21, a lens 22, and an interference image capturing camera 23.

The diaphragm 21 and the lens 22 allow the corneal reflection light R2 incident from the half mirror A14 to exit therefrom toward the interference image capturing camera 23.

The interference image capturing camera 23 includes a CMOS or CCD imaging element, and takes an image of the corneal reflection light R2 incident from the lens 22 to output an imaging signal of a corneal reflection image to the control unit 10.

A fixation lamp 24 is a light source that fixes the position of the subject's eye E by guiding the subject's gaze for accurate observation and photographing of the state of the subject's eye E. A light emitting diode (LED) light source or a halogen lamp can be used as the fixation lamp 24. The light L2 emitted from the fixation lamp 24 passes through the half mirror B15 and the second lens group 16, is reflected from the half mirror C17, and enters the subject's eye E through the first lens group 18. Specifically, the subject's eye E can be irradiated with the light L2 from the fixation lamp 24 through the first lens group 18 included in an alignment adjustment system, which will be described later.

The alignment adjustment system is a mechanism including an alignment adjustment unit 40, such as a servo motor, that makes the first lens group 18 movable. Driving the servo motor electrically connected to the control unit 10 to move the first lens group 18 makes it possible to adjust the relative position between the subject's eye E and the first lens group 18 in an optical axis direction, and to adjust the alignment of the optical system. That is, the alignment of the light of the fixation lamp 24 irradiated through the first lens group 18 can also be adjusted at the same time. This allows the light L2 from the fixation lamp 24 to be focused on the fundus (retina) of the subject's eye E. Therefore, blurring, caused by the movement of an eyeball, of an image captured by, for example, the anterior segment camera 20 or the interference image capturing camera 23 can be reduced while maintaining the focus on the anterior segment.

The alignment adjustment system is used for measuring the alignment of the subject's eye E and the first lens group 18 in the optical axis direction by an optical lever method. The alignment adjustment system performs an adjustment (alignment adjustment) of the relative position between the subject's eye E and the optical system by moving the first lens group 18 using the result of the alignment measurement. The focus adjustment system includes an alignment light source 4a and an alignment reflection light receiving unit 4b. The alignment reflection light receiving unit 4b may be a linear sensor such as a CCD, a CMOS, and a PSD (position sensitive detector). Alternatively, the alignment reflection light receiving unit 4b may have a plurality of light-receiving regions.

The alignment light source 4a is arranged between an objective lens 18a of the first lens group 18 and the half mirror C17. The alignment light source 4a is arranged away from an optical axis center of the anterior segment camera 20. The alignment light source 4a emits the alignment light A1. The alignment light A1 emitted enters the corneal surface of the cornea Ea in an oblique direction relative to the corneal surface via the objective lens 18a of the first lens group 18. When the first lens group 18 is in alignment with the cornea Ea of the subject's eye E, the alignment reflection light receiving unit 4b can receive alignment reflection light A2, which is the reflection from the surface of the cornea Ea. Accordingly, whether the subject's eye E and the first lens group 18 are aligned or not can be determined based on the determination as to whether the alignment reflection light receiving unit 4b receives the alignment reflection light A2 at a certain appropriate position or not. The alignment reflection light receiving unit 4b outputs a light receiving signal indicative of the receipt of the reflected light to the control unit 10.

A ghost removing light source 4 may be, for example, a light emitting diode (LED) light source or a halogen lamp, and is able to emit illumination light L3 toward a corneal surface of a cornea Ea of a subject's eye E. The ghost removing light source 4 has an optical axis that is shifted from the optical axis of the first lens group 18, which will be described later (second illumination optical system 1d).

The control unit 10 is electrically connected to the ghost removing light source 4, the alignment light source 4a, the alignment reflection light receiving unit 4b, the first illumination light source 11, the anterior segment camera 20, the interference image capturing camera 23, the fixation lamp 24, and the alignment adjustment unit 40.

The control unit 10 detects, based on the inputted image data of the corneal reflection light R2 (corneal reflection image), wavelength characteristics of the interference image at each position of the corneal reflection image so that the thickness of the tear fluid film at each position on the corneal surface can be detected. The tear fluid film herein refers to an oil layer (lipid layer), an aqueous layer, and a mucinous layer, or a combination of these layers.

The control unit 10 can switch between the first illumination light source 11 and the ghost removing light source 4 (second illumination light source) to irradiate the eye with the illumination light. This enables switching between the mode for reducing ghost and the mode for irradiating the center of the subject's eye E with light in accordance with the examination to be performed.

The first illumination light source 11 of the present disclosure is a light source made of a single LED. Therefore, even when the illumination light L1 emitted from the first illumination light source 11 reaches the cornea Ea through the first lens group 18, the shape of a single light source is projected.

In opposition to this, a comparative example will be described now where a plurality of light sources including nine LEDs arranged in a matrix of 3×3 are used as the first illumination light source 11, for example. Thus, when the illumination light emitted from the first illumination light source 11 of the comparative example reaches the cornea Ea through the first lens group 18, the light from the plurality of LEDs, i.e., point light sources, is condensed by the first lens group 18 to generate dark portions adjacent to the plurality of LEDs. That is, illuminance difference in the shape of stripes is projected on the cornea Ea as blurred stripes. Therefore, the stripes of the illuminance difference are also generated in the corneal reflection light R1 reflected from the cornea Ea. As a result, the illumination on the cornea Ea of the subject's eye E has shades, and the thickness of the tear fluid on the corneal surface may not be accurately measured.

On the other hand, according to the present disclosure, measurement of the cornea Ea is performed under illumination from a single light source. This makes it possible to accurately measure the thickness of the tear fluid on the corneal surface without generating the stripes of the illuminance difference on the cornea.

Further, the light from the fixation lamp 24 is superimposed and irradiated via the first lens group that is an optical system of the alignment adjustment system, so that the blurring caused by the movement of the eyeball can be reduced by maintaining the focus state, and interference fringes formed by the tear fluid film of the cornea Ea of the subject's eye E can be accurately observed.

Furthermore, irradiating the illumination light L3 from the ghost removing light source 4 makes it possible to shift the position of ghost generated by reflection of the illumination light L3 at the anterior segment away from the optical axis of the anterior segment camera 20. In this manner, ghost can be kept from entering the field of view of the anterior segment camera 20. Hence, it is possible to perform an accurate examination of a cornea or tear fluid film around the center of a subject's eye E, and acquisition of a more accurate corneal image.

Note that the ghost removing light source 4 (second illumination light source) from which the illumination light L3 is emitted may have an optical axis along which the illumination light L3 enters the cornea Ea of the subject's eye E from below. Alternatively, the ghost removing light source 4 (second illumination light source) may be arranged to have an optical axis that extends in a horizontal direction with respect to an optical axis center of the first lens group 18.

Next, the half mirror B15 (first mirror) and the half mirror A14 (second mirror) will be described below. Each of the half mirrors B15 and A14 has a coating layer on its reflection surface. Further, the half mirrors B15 and A14 are configured such that their reflection surfaces form a right angle. That is, the half mirrors B15 and A14 are configured such that light is reflected and exits from the half mirror A14 toward the incident side from which the corneal reflection light R2 enters.

Figure 2:
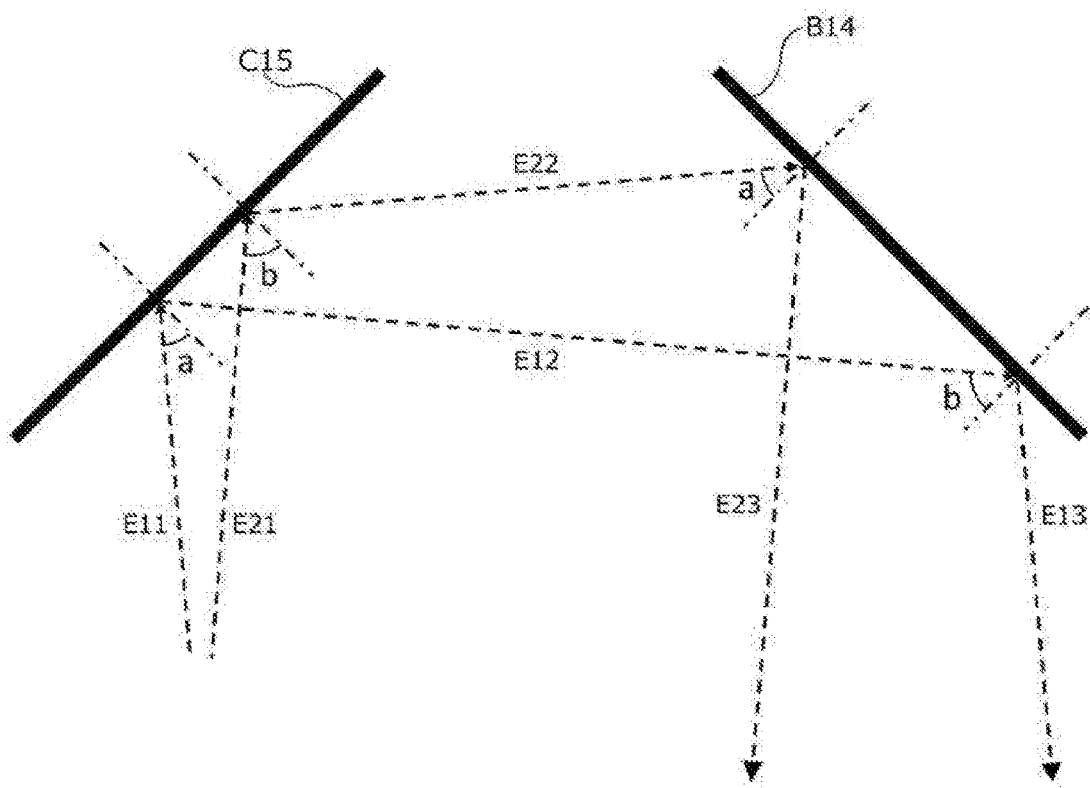
FIG. 2 is a schematic view illustrating a configuration of half mirrors A and B of the optical system of the ophthalmologic apparatus according to the embodiment of the present disclosure.

FIG. 2 is a schematic view illustrating a configuration of half mirrors B15 and A14 of the optical system of the ophthalmologic apparatus according to the embodiment of the present disclosure. FIG. 2 illustrates the half mirror B15 (first mirror) and the half mirror A14 (second mirror) of the optical system of the ophthalmologic apparatus according to the embodiment of the present disclosure, and lights between them. The corneal reflection light R2 that has passed through the second lens group 16 enters the half mirror B15 as diffused light. This light will be described below by way of representative light beams, namely, a light beam E11 and a light beam E21.

The light beam E11 enters the half mirror B15 at an incident angle a. The light beam E11 is reflected from the half mirror B15, and exits as a light beam E12. The light beam E12 enters the half mirror A14 at an incident angle b. The light beam E12 is reflected from the half mirror A14, and exits toward the lens 22 and the interference image capturing camera 23 as a light beam E13. Next, the light beam E21 enters the half mirror B15 at an incident angle b. The light beam E21 is reflected from the half mirror B15, and exits as a light beam E22. The light beam E22 enters the half mirror A14 at an incident angle a. The light beam E22 is reflected from the half mirror A14, and exits toward the lens 22 and the interference image capturing camera 23 as a light beam E23.

It will be considered below a relationship between the incident light beams E11, E21 and the exiting light beams E13, E23. The incident light beam E11 is reflected once at the angle a from one of the half mirrors, once at the angle b from the other, and becomes the light beam E13. Similarly, the incident light beam E21 is reflected once at the angle b from one of the half mirrors, once at the angle a from the other, and becomes the light beam E23. Reflectance R, or wavelength dependence $dR/d\lambda$ of the reflectance, of each mirror generally varies depending on the incident angle with respect to the half mirror. Thus, each of the light beams E13 and E23 that will finally exit has been reflected at the angles a and b with respect to the incident light beam. Therefore, when passing through the pair of half mirrors, each light beam has its unevenness in light intensity and wavelength dependence (chromatic aberration) reduced. This makes it possible to reduce the amount of change in light intensity distribution or in wavelength dependence (color irregularities) in an image of the corneal reflection light R2 taken by the interference image capturing camera 23. In particular, the light beams E13 and E23 are reflected at the same angles (a, b and b, a) in combination, and thus, the difference between the light beams E13 and E23 in the total reflectance R, or wavelength dependence dR/dλ of the reflectance is canceled out.

With the half mirror B15 (first mirror) and the half mirror A14 (second mirror) configured to be arranged in this relationship, in which the corneal reflection light R2 that enters and is reflected from the half mirror B15, and then enters and is reflected from the half mirror A14 exits toward the incident side from which the corneal reflection light R2 enters the half mirror B15, i.e., in the direction toward the place where the second lens group 16 is arranged, the above-described advantage is obtained.

Figure 3:
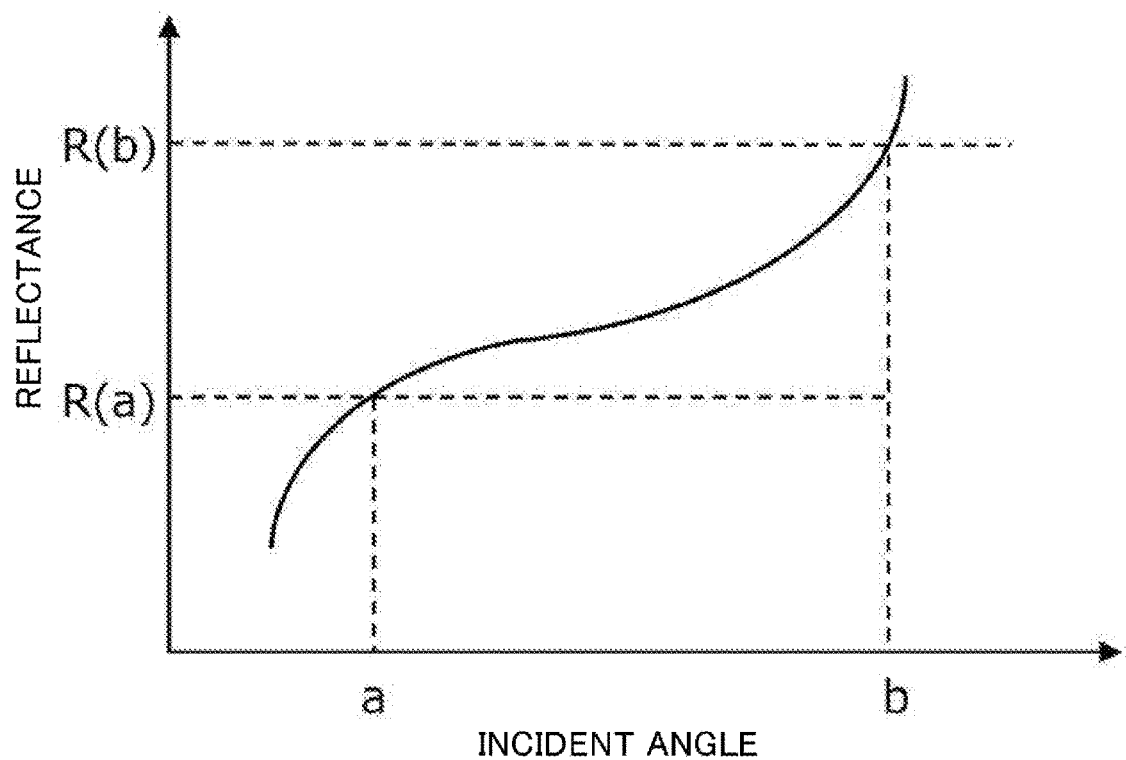
FIG. 3 is a graph illustrating a reflection characteristic of a mirror according to the embodiment of the present disclosure.
Figure 4:
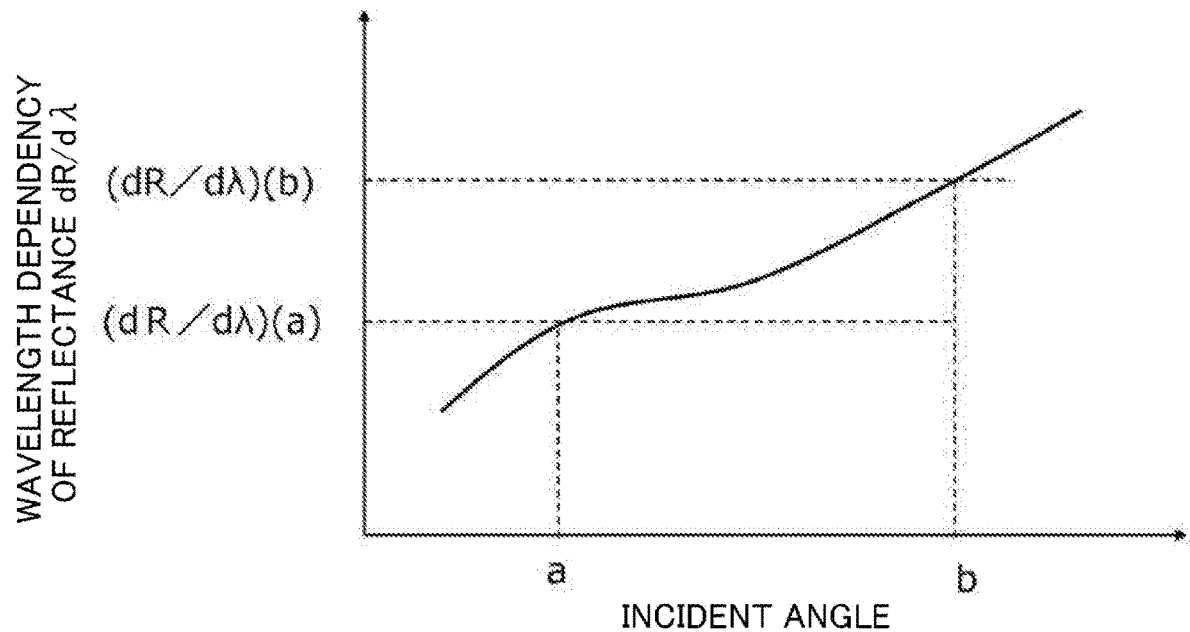
FIG. 4 is a graph illustrating wavelength dependence of reflectance of the mirror according to the embodiment of the present disclosure.

FIGS. 3 and 4 are graphs each illustrating the characteristics of the mirror of each of the half mirrors according to the embodiment of the present disclosure. Hereinafter, the mirror includes the above-described half mirror. FIG. 3 is a graph in which a horizontal axis shows the incident angle, and a vertical axis the reflectance R. The mirror has, as one of its optical characteristics, the reflectance R that varies depending on the incident angle. The difference in illuminance derived from the reflectance of each mirror is generated in accordance with the incident angle with respect to the mirror. Thus, each of the light beams E13 and E23 that will finally exit has been reflected at the angles a and b with respect to the incident light beam. Therefore, the illuminance at the position on the mirror where the light beam enters is made uniform. The light beam system of the light beams E11 to E13 is emitted with a reflectance of R(a)×R(b), while the light beam system of the light beams E21 to E23 is emitted with a reflectance of R(b)×R(a). Thus, the finally obtained illuminances of the both systems are identical to each other. In other words, this can reduce the change in the unevenness in light intensity in the image generated from the corneal reflection light R2 taken by the interference image capturing camera 23. FIG. 4 is a graph in which a horizontal axis shows the incident angle, and a vertical axis the wavelength dependence dR/dλ of the reflectance. The mirror has, as one of its optical characteristics, the wavelength dependence dR/dλ of the reflectance that varies depending on the incident angle. The wavelength dependence dR/dλ of the light intensity derived from the reflectance of each mirror is generated in accordance with the incident angle with respect to the mirror. Thus, each of the light beams E13 and E23 that will finally exit has been reflected at the angles a and b with respect to the incident light beam. Therefore, wavelength dependence of the light intensity at the position on the mirror where the light beam enters is made uniform. Specifically, this can reduce the change in the wavelength dependence of the light intensity in the image generated from the corneal reflection light taken by the interference image capturing camera 23. In FIGS. 3 and 4, the values on the vertical axis are plotted to increase relative to the incident angles a and b, but the present invention is not limited thereto, as long as their positions on the vertical axis are different.

Figure 5:
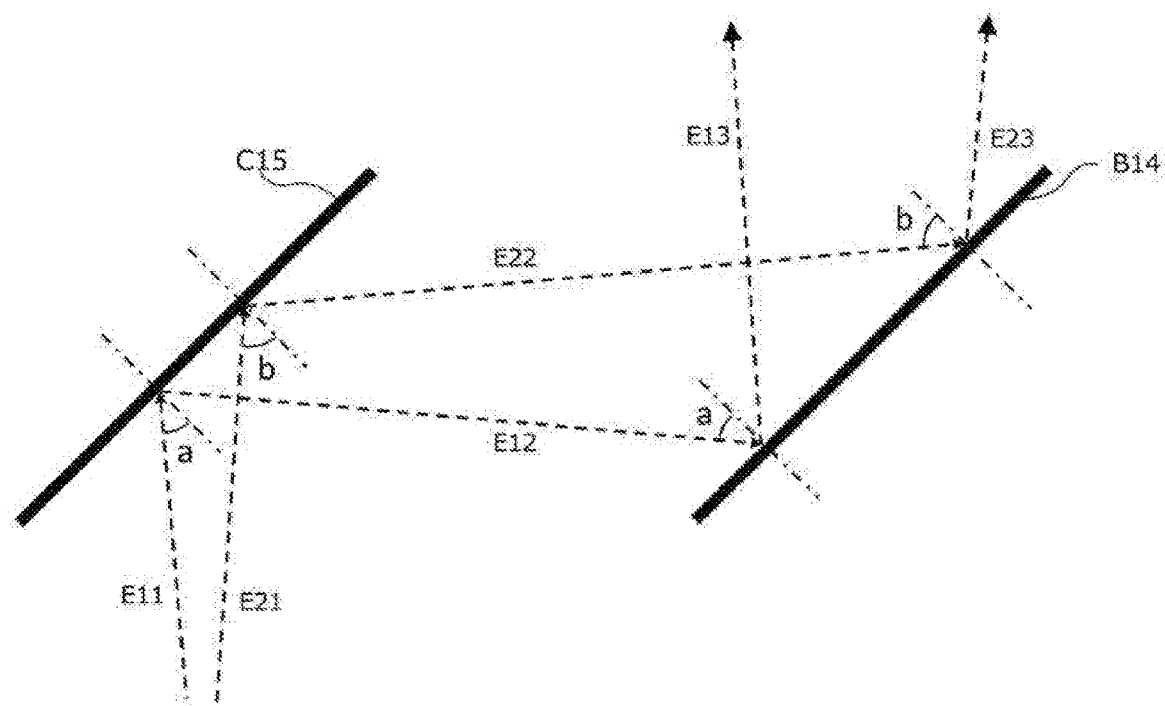
FIG. 5 is a schematic view illustrating a configuration of half mirrors A and B of an optical system of an ophthalmologic apparatus according to a comparative example of the present disclosure.

FIG. 5 is a schematic view illustrating a configuration of half mirrors B15 and A14 of an optical system of the ophthalmologic apparatus according to the comparative example of the present disclosure. FIG. 5 illustrates a state in which the orientation of the half mirror A14 (second mirror) is inverted in the up-and-down direction compared to that in the optical system illustrated in FIG. 2. Specifically, in this configuration, the light is reflected and exits from the half mirror A14 toward the side different from the incident side from which the corneal reflection light R2 enters. The corneal reflection light R2 that has passed through the second lens group 16 enters the half mirror B15 as diffused light. This light will be described below by way of representative light beams, namely, a light beam E11 and a light beam E21.

The light beam E11 enters the half mirror B15 at an incident angle a. The light beam E11 is reflected from the half mirror B15, and exits as a light beam E12. The light beam E12 enters the half mirror A14 at an incident angle a. The light beam E12 is reflected from the half mirror A14, and exits toward the lens 22 and the interference image capturing camera 23 as a light beam E13. Next, the light beam E21 enters the half mirror B15 at an incident angle b. The light beam E21 is reflected from the half mirror B15, and exits as a light beam E22. The light beam E22 enters the half mirror A14 at an incident angle b. The light beam E22 is reflected from the half mirror A14, and exits toward the lens 22 and the interference image capturing camera 23 as a light beam E23.

In this manner, it will be considered below a relationship between the incident light beams E11, E21 and the exiting light beams E13, E23. The incident light beam E11 is reflected twice at the incident angle a from the half mirrors, and becomes the light beam E13. Similarly, the incident light beam E21 is reflected twice at the incident angle b from the half mirrors, and becomes the light beam E23. The difference in light intensity or in wavelength dependence of the light intensity caused on a reflection surface of each mirror is generated in accordance with the incident angle with respect to the half mirror. Thus, the light beam E13 that will finally exit has been reflected twice at the angle a, and the light beam E23 that will finally exit has been reflected twice at the angle b, with respect to the incident light beam. Therefore, the difference in light intensity or in wavelength dependence of the light intensity becomes significant with respect to the position on the half mirror where the light beam enters. Similarly, this increases the unevenness in light intensity or in wavelength dependence of the light intensity in an image generated from the corneal reflection light R2 taken by the interference image capturing camera 23.

Figure 6:
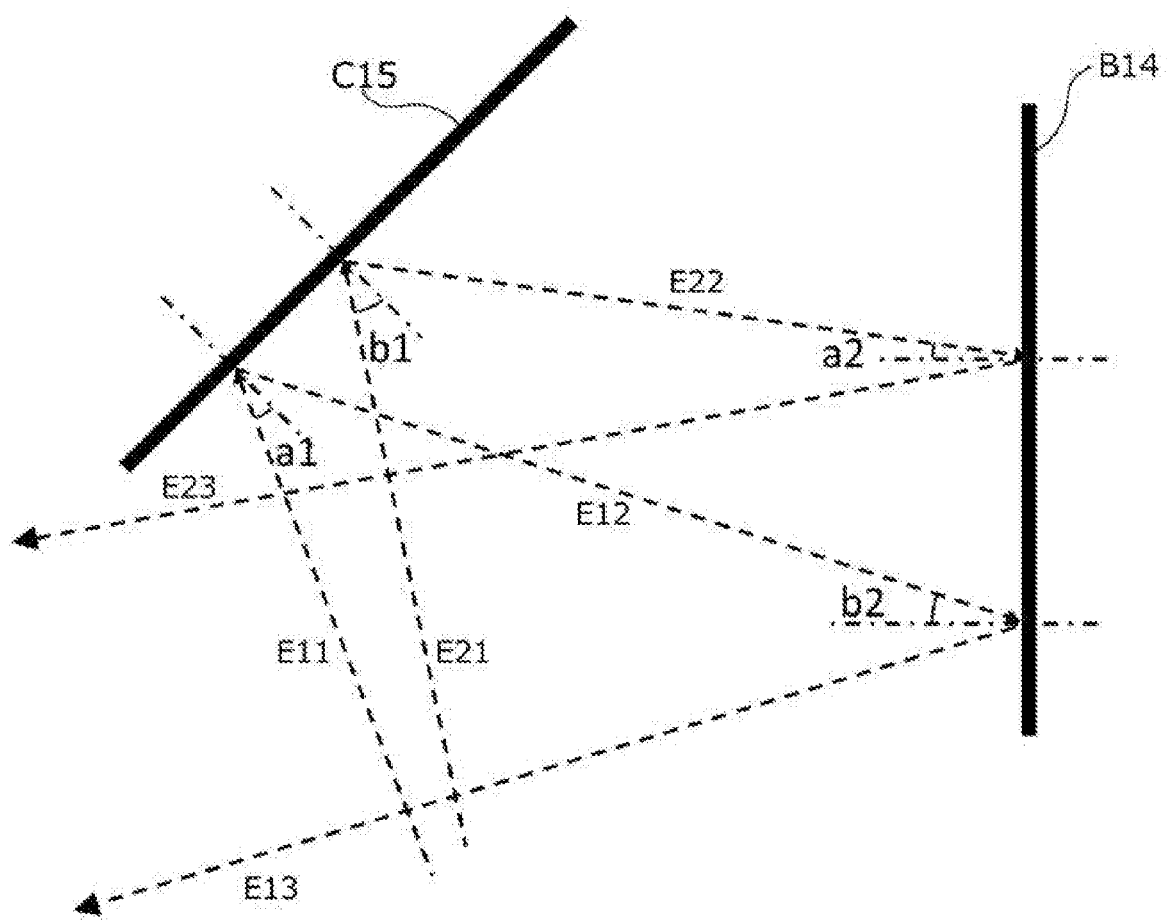
FIG. 6 is a schematic view illustrating a configuration of half mirrors A and B of an optical system of an ophthalmologic apparatus according to a variation of the embodiment of the present disclosure.

As can be seen in the foregoing, the case has been described where the half mirrors B15 and A14 are arranged to form a right angle. However, the advantage of the present disclosure can be obtained also in another configuration. FIG. 6 illustrates the half mirror B15 (first mirror) and the half mirror A14 (second mirror) of an optical system of an ophthalmologic apparatus according to a variation of the embodiment of the present disclosure, and lights between them. The half mirrors B15 and A14 have their reflection surfaces facing each other to form an angle of 45 degrees. That is, the half mirrors B15 and A14 are configured such that light is reflected and exits from the half mirror A14 toward the incident side from which the corneal reflection light R2 enters. In FIG. 6, the corneal reflection light R2 that has passed through the second lens group 16 enters the half mirror B15 as diffused light. This light will be described below by way of representative light beams, namely, a light beam E11 and a light beam E21.

The light beam E11 enters the half mirror B15 at an incident angle a1. The light beam E11 is reflected from the half mirror B15, and exits as a light beam E12. The light beam E12 enters the half mirror A14 at an incident angle b2. The light beam E12 is reflected from the half mirror A14, and exits toward the lens 22 and the interference image capturing camera 23 as a light beam E13. Next, the light beam E21 enters the half mirror B15 at an incident angle b1. The light beam E21 is reflected from the half mirror B15, and exits as a light beam E22. The light beam E22 enters the half mirror A14 at an incident angle a2. The light beam E22 is reflected from the half mirror A14, and exits toward the lens 22 and the interference image capturing camera 23 as a light beam E23.

It will be considered below a relationship between the incident light beams E11, E21 and the exiting light beams E13, E23. The incident light beam E1 is reflected once at the angle a1 from one of the half mirrors, once at the angle b2 from the other, and becomes the light beam E13. Similarly, the incident light beam E21 is reflected once at the angle b1 from one of the half mirrors, once at the angle a2 from the other, and becomes the light beam E23. As described above, reflectance R, or wavelength dependence dR/dλ of the reflectance, of each mirror generally varies depending on the incident angle with respect to the half mirror. In FIG. 6, the relationships of the angle a1<the angle b1, and the angle a2<the angle b2 are established. The light beam E13 that will finally exit has been reflected at the angles a1 and b2, and the light beam E23 at the angles b and a2. Therefore, when passing through the pair of half mirrors, each light beam has its light intensity I and wavelength dependence dI/dλ of the light intensity reduced. This makes it possible to reduce the unevenness in light intensity or in wavelength dependence of the light intensity in an image generated from the corneal reflection light R2 taken by the interference image capturing camera 23.

Figure 7:
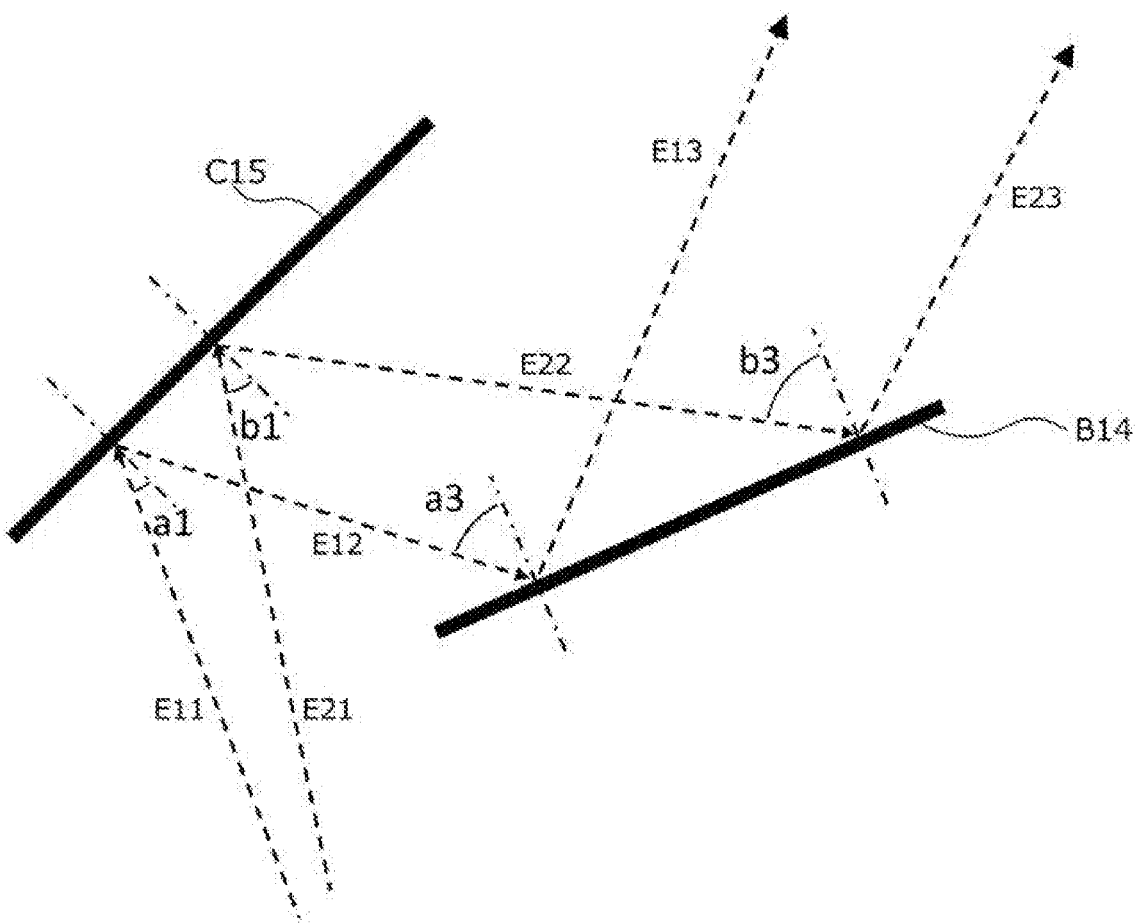
FIG. 7 is a schematic view illustrating a configuration of half mirrors A and B of an optical system of an ophthalmologic apparatus according to a comparative example of the variation of the present disclosure.

As a comparison, as shown in FIG. 7, for example, it will be considered below a configuration in which the light is reflected and exits from the half mirror A14 toward the side different from the incident side from which the corneal reflection light R2 enters. In this case, the incident light beam E11 is reflected once at the angle a1 from one of the half mirrors, once at the angle a3 from the other to become the light beam E13, and the incident light beam E21 is reflected once at the angle b1 from one of the half mirrors, once at the angle b3 from the other to become the light beam E23. Thus, the angle a1<the angle b1, and the angle a3<the angle b3 are established. Therefore, when passing through the pair of half mirrors, each light beam has its unevenness in light intensity and unevenness in wavelength dependence of the light intensity increased.

As can be seen in the foregoing, in a configuration where the light is reflected and exits from the half mirror A14 toward the incident side from which the corneal reflection light R2 enters, the relationship between the half mirror B15 (first mirror) and the half mirror A14 (second mirror) makes it possible to reduce the unevenness in light intensity and unevenness in wavelength dependence of the light intensity in the image generated from the corneal reflection light R2.

As will be apparent from the comparative example, the configuration of the present disclosure can reduce the unevenness in light intensity and unevenness in wavelength dependence of the light intensity in the image formed by the optical system. Therefore, an ophthalmologic apparatus can be provided which is capable of reducing unevenness in light intensity of the corneal image and unevenness in wavelength dependence of the light intensity in an examination of the subject's eye, so that the film thickness of the tear fluid film can be precisely measured.

In the present embodiment, the description has been made taking the diffused light beam as an example, but the same advantage is also obtained in the case of a converging light beam. In the present embodiment, the description has been made using the half mirror as the first or second mirror. However, a general total reflection mirror can also be used. The mirror desirably has a flat reflection surface.

What is claimed is:

1. An ophthalmologic apparatus, comprising:
   an objective lens that faces a subject's eye;
   a first illumination optical system that irradiates a cornea of the subject's eye with illumination light emitted from a first illumination light source along an optical axis overlapping an optical axis center of the objective lens; and
   a corneal measurement optical system having an imaging element that takes an image of a corneal reflection light, which is a reflection of the illumination light, through the objective lens, and outputs an imaging signal, wherein
   the first illumination optical system includes a first mirror arranged near the objective lens, and a second mirror arranged near the imaging element, and
   the first and second mirrors are configured such that the corneal reflection light that enters and is reflected from the first mirror, and then enters and is reflected from the second mirror exits toward an incident side from which the corneal reflection light enters a reflection surface of the first mirror,
   the second mirror allows part of the illumination light incident from the first illumination light source to pass therethrough and exit therefrom toward the first mirror and reflects the corneal reflection light incident from the first mirror toward the corneal measurement optical system, and
   the first mirror allows the illumination light incident from the second mirror to exit therefrom toward the subject's eye side and allows the corneal reflection light incident from the subject's eye side to exit therefrom toward the second mirror.

2. The ophthalmologic apparatus of claim 1, wherein the first and second mirrors have flat reflection surfaces.

3. The ophthalmologic apparatus of claim 1, wherein the first mirror and/or the second mirror is a half mirror.

4. The ophthalmologic apparatus of claim 1, wherein the corneal measurement optical system is configured such that the first and second mirrors form a right angle between their reflection surfaces.

5. The ophthalmologic apparatus of claim 1, wherein in the corneal measurement optical system, the corneal reflection light that enters the first mirror is converging light or diffused light.

6. The ophthalmologic apparatus of claim 1, wherein the first illumination optical system includes a single light source only.

7. The ophthalmologic apparatus of claim 6, wherein the single light source is a bullet-shaped LED.

8. The ophthalmologic apparatus of claim 1, further comprising:
   an alignment adjustment unit that adjusts a position of the objective lens in order to adjust a relative position between the subject's eye and the objective lens; and
   a fixation lamp including a light source different from the first illumination light source,
   wherein
   the fixation lamp emits light that focuses on a retina of the subject's eye through the objective lens.

9. The ophthalmologic apparatus of claim 1, further comprising:
   a second illumination optical system that irradiates the cornea of the subject's eye with illumination light emitted from a second illumination light source along an optical axis center different from the optical axis center of the objective lens; and a control unit that controls the first illumination light source and the second illumination light source, wherein the control unit is able to switch between the first illumination light source and the second illumination light source to irradiate the cornea with the illumination light.

10. The ophthalmologic apparatus of claim 9, wherein the second illumination light source emits the illumination light to irradiate the cornea of the subject's eye with the illumination light without passing through the objective lens.

* * * * *